(12) United States Patent
Mazzoni

(10) Patent No.: US 7,258,119 B2
(45) Date of Patent: Aug. 21, 2007

(54) DISPENSER

(75) Inventor: Paolo Mazzoni, Milan (IT)

(73) Assignee: Glaxo Group Limited, Greenford (GB)

( * ) Notice: Subject to any disclaimer, the term of this patent is extended or adjusted under 35 U.S.C. 154(b) by 698 days.

(21) Appl. No.: 10/474,493

(22) PCT Filed: Apr. 10, 2002

(86) PCT No.: PCT/GB02/01660

§ 371 (c)(1),
(2), (4) Date: Oct. 8, 2003

(87) PCT Pub. No.: WO02/083218

PCT Pub. Date: Oct. 24, 2002

(65) Prior Publication Data

US 2004/0153033 A1    Aug. 5, 2004

(30) Foreign Application Priority Data

Apr. 10, 2001 (GB) .................................. 0109002.6

(51) Int. Cl.
*A61M 15/00* (2006.01)
*A61M 16/00* (2006.01)
*A61M 16/10* (2006.01)
*A61M 11/00* (2006.01)

(52) U.S. Cl. .......................... 128/203.21; 128/203.12; 128/200.14; 128/200.22

(58) Field of Classification Search ............ 128/200.13, 128/200.14, 200.18, 200.19, 200.21, 200.22, 128/203.12, 203.21, 203.22, 204.12; 222/83, 222/386; 604/19, 48, 57, 58, 59, 514, 181, 604/187

See application file for complete search history.

(56) References Cited

U.S. PATENT DOCUMENTS

| 4,896,832 | A | * | 1/1990 | Howlett ....................... 239/322 |
| 5,104,380 | A | * | 4/1992 | Holman et al. ............. 604/117 |
| 5,137,516 | A | | 8/1992 | Rand et al. |
| 5,331,954 | A | * | 7/1994 | Rex et al. ............... 128/200.22 |
| 6,109,479 | A | * | 8/2000 | Ruckdeschel ................. 222/82 |
| 6,257,454 | B1 | | 7/2001 | Ritsche |
| 6,641,560 | B1 | * | 11/2003 | Bechtold et al. ............ 604/136 |
| 6,708,846 | B1 | * | 3/2004 | Fuchs et al. .................. 222/82 |

FOREIGN PATENT DOCUMENTS

| EP | 0518416 | 12/1992 |
| EP | 0 546 607 A1 | 6/1993 |
| EP | 0546607 | 6/1993 |
| EP | 0953515 | 11/1999 |
| WO | 97/42992 | 11/1997 |
| WO | 00 35516 A | 6/2000 |

* cited by examiner

Primary Examiner—Justine R. Yu
Assistant Examiner—Kristen Matter
(74) Attorney, Agent, or Firm—Alice P. Bradney

(57) ABSTRACT

A dispensing apparatus for dispensing a unit dose of a pharmaceutical substance, in particular for intranasal administration, is described. The apparatus includes a nozzle unit having a safety cap thereon and an actuating device. The safety cap has legs, which can locate within the actuating device. Upon mounting the nozzle unit on the actuating device, the legs on the safety cap push down a ram in the device against the action of a spring, until the head of the ram engages over a shoulder. The ram is released by depression of a button on the device and by relative movement of two parts of the device.

18 Claims, 11 Drawing Sheets

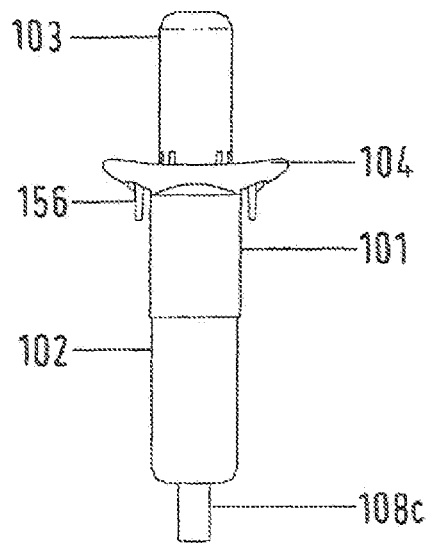
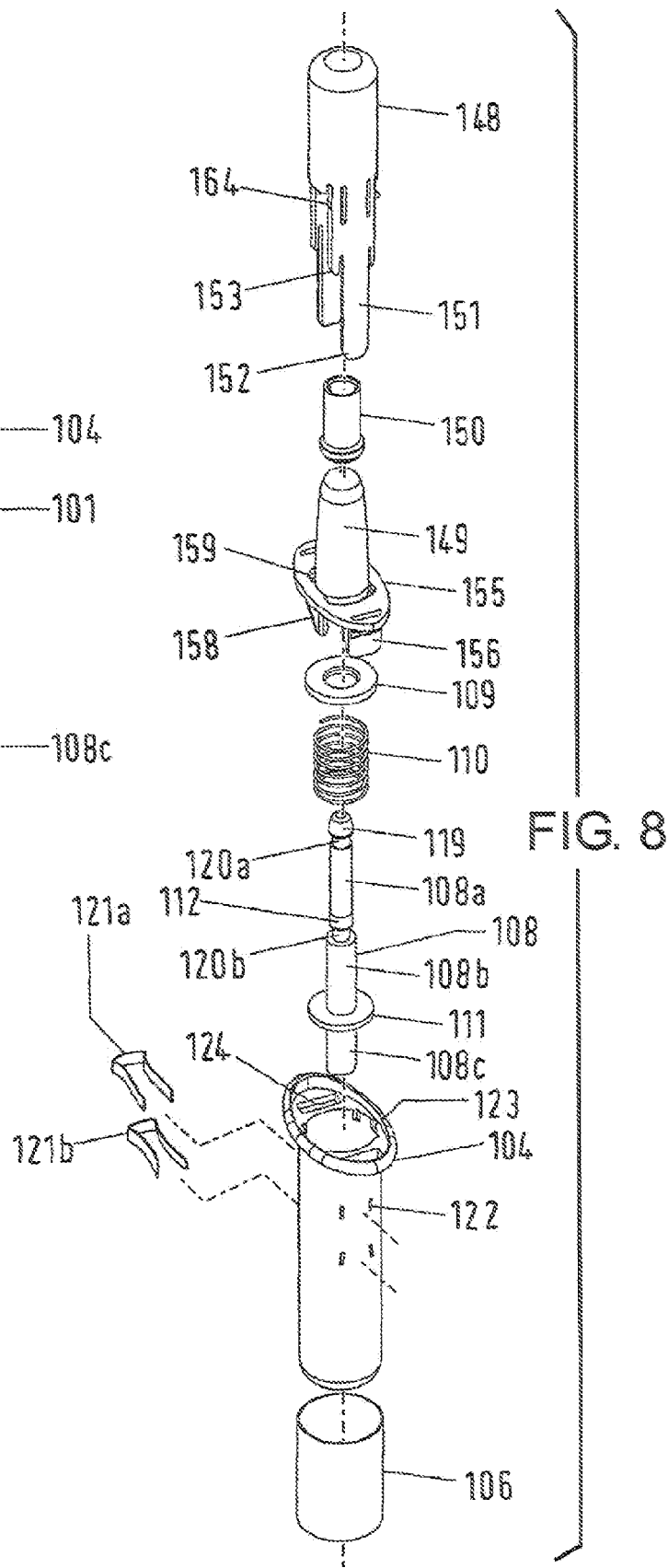

FIG. 10b
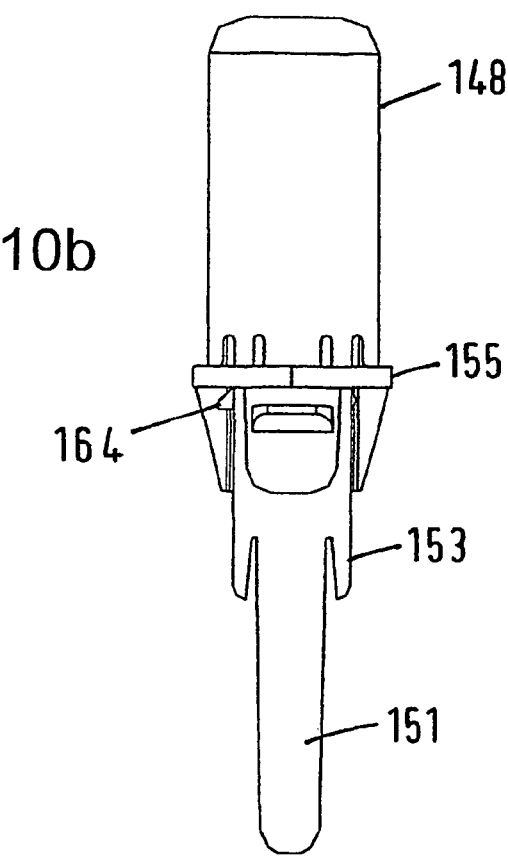
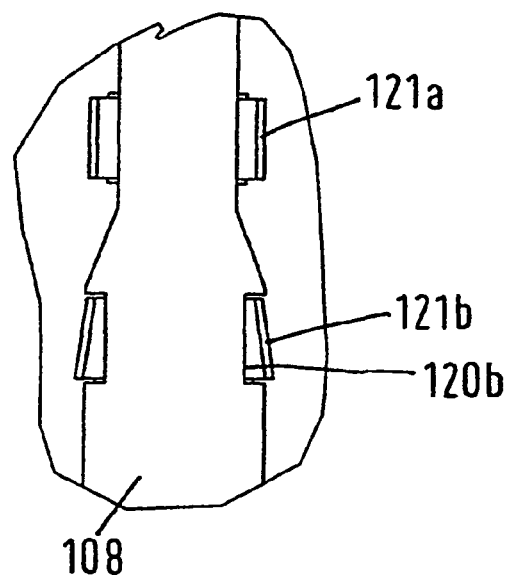

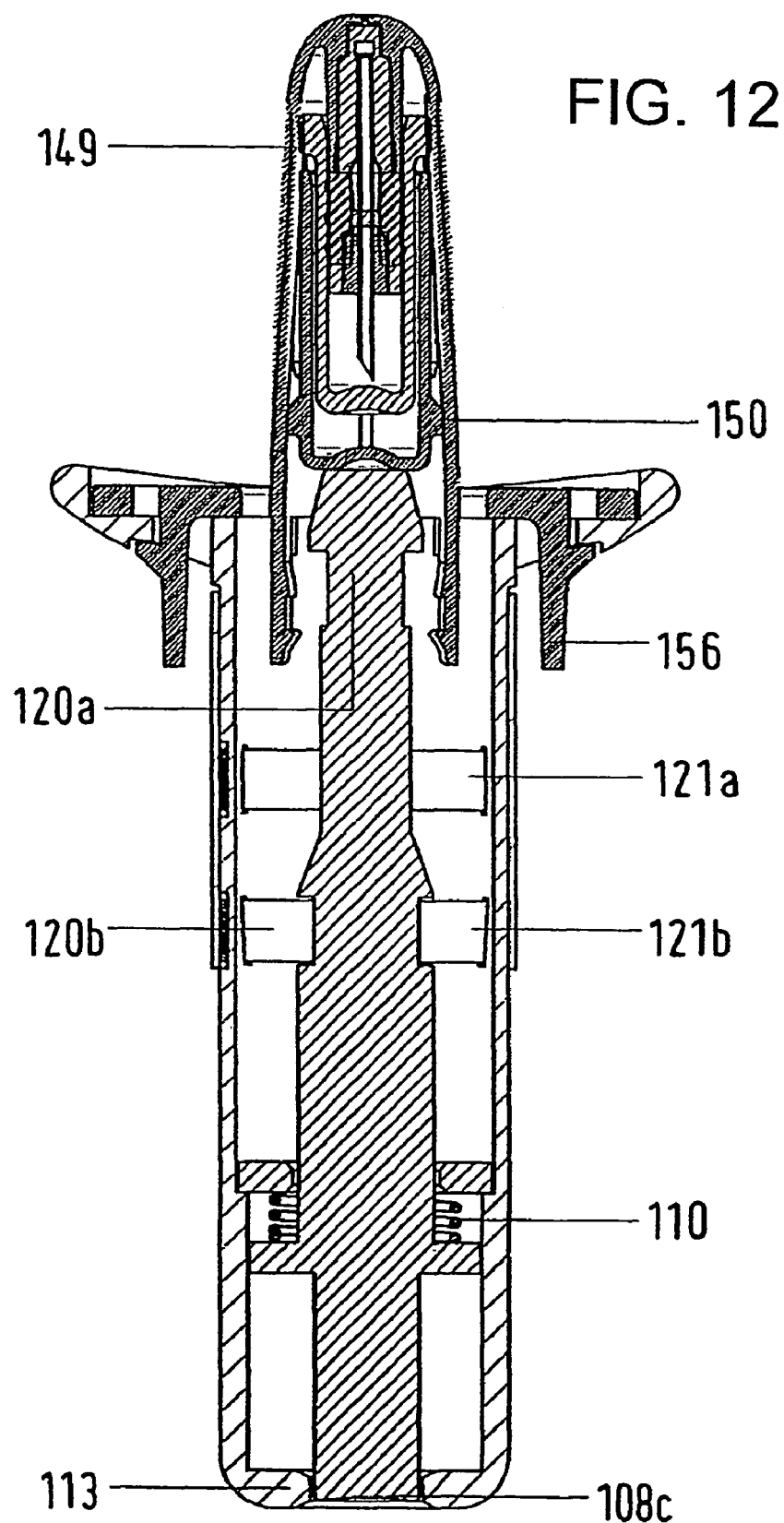

DISPENSER

This application is filed pursuant to 35 U.S.C. § 371 as a U.S. National Phase Application of International Patent Application Serial No. PCT/GB02/01660 filed Apr. 10, 2002, which claims priority from Great Britain Application No. 0109002.6 filed in the United Kingdom on Apr. 10, 2001.

The present invention relates to a device for dispensing a pharmaceutical substance. In particular, the invention relates to a device for dispensing a pharmaceutical substance by intranasal administration.

European Patent Publication No. EP-A-0546607 in the name of Glaxo Group Limited discloses a dispenser for manual discharge of a single dose of a flowable substance. The device consists of a casing with a nozzle member and shoulders to the sides of the nozzle member. The nozzle member has a piston extending inwardly from an outlet opening, the piston having at least one discharge channel. A vial of the pharmaceutical substance to be dispensed is mounted on the piston member with a stopper arranged across the vial to seal in the substance. The piston includes a hollow needle, so that on pressing of the vial onto the piston member, the stopper is pierced by the needle to allow the substance to be expelled through the discharge channel and out of the nozzle opening. The described device is a one-use only device and is intended to be discarded after use.

International Patent Publication No. WO97/42992 in the name of Glaxo Wellcome Australia Limited discloses a device for dispensing a unit dose of a pharmaceutical substance. The device includes a body member which has a discharge system which can be operated by the user to effect discharge of the pharmaceutical substance, in particular by means of a spring loaded air piston which injects air into a container of the substance to discharge it. A number of nozzle assemblies are provided, each nozzle assembly including a container of a unit dose of the pharmaceutical substance. A single nozzle assembly is mounted on the body member and in one embodiment a driving spring for the air piston is loaded with spring energy by the action of mounting the nozzle assembly on the body. After the spring is released, and the substance thus discharged, the nozzle assembly is discarded and a fresh nozzle assembly can be mounted on the body as required.

U.S. Patent Publication No. U.S. Pat. No. 5,137,516 again in the name of Glaxo Group Limited describes a device for administering a dose of a pharmaceutical substance, in particular by self-injection by the user. The device holds a syringe of the pharmaceutical substance and the syringe is pressed against the user's skin by a spring force, the spring force being released by relative movement of cooperating sleeves of the device and by pressure on a button on one end of the device. The spring can be placed into a ready-to-use state by loading of the syringe onto the device. The device may be provided in a carry case, along with a small number of spare syringes.

There remains a need for a pharmaceutical dispensing device which is easy and convenient to use.

According to the invention there is provided a device for dispensing a pharmaceutical substance comprising: a disposable unit including a dose of the pharmaceutical substance, the unit having a protective cap;

a body member on which the unit can be removably mounted, the body member including an actuation member for dispensing the pharmaceutical substance from the unit, the actuation member being movable between a retracted position and an advanced position in which the pharmaceutical substance is dispensed; and wherein the protective cap has at least one surface which can operatively engage the body member so that on mounting of the unit on the body member the actuation member is moved from the advanced to the retracted position.

The invention thus has the advantage that an already emptied unit, with the cap removed, cannot be used to bring the device to an actuation condition. Correct usage of the device is therefore assured, with only a fresh single-dose unit being fitted by the user.

Preferably, the surface of the protective cap is provided at the end of one or more depending legs of the protective cap. On mounting of the unit, the legs can penetrate the body member to push or release the actuation member to its retracted position.

Advantageously, the protective cap or the body member has a blocking part which blocks the actuation member from movement to the advanced position until the cap is removed. Premature actuation of the device is thus avoided.

Preferred embodiments of the invention are described in more detail below, by example only, with reference to the accompanying drawings:

FIG. 3 is an exploded perspective view of the unit which contains the pharmaceutical substance;

FIG. 7 is an elevational view of a device for dispensing a pharmaceutical substance in accordance with a second embodiment of the invention;

FIG. 8 is an exploded perspective view of the device of FIG. 7;

FIG. 10a is a sectional view similar to that of FIG. 9, but showing the unit containing the pharmaceutical substance in its mounted position, with the cap on;

FIG. 10b is a detail of the view of FIG. 10a, showing the effect of the mounting of the unit;

FIG. 12 is a similar sectional view showing the device in a used condition, with the pharmaceutical substance dispensed.

Figure 1:
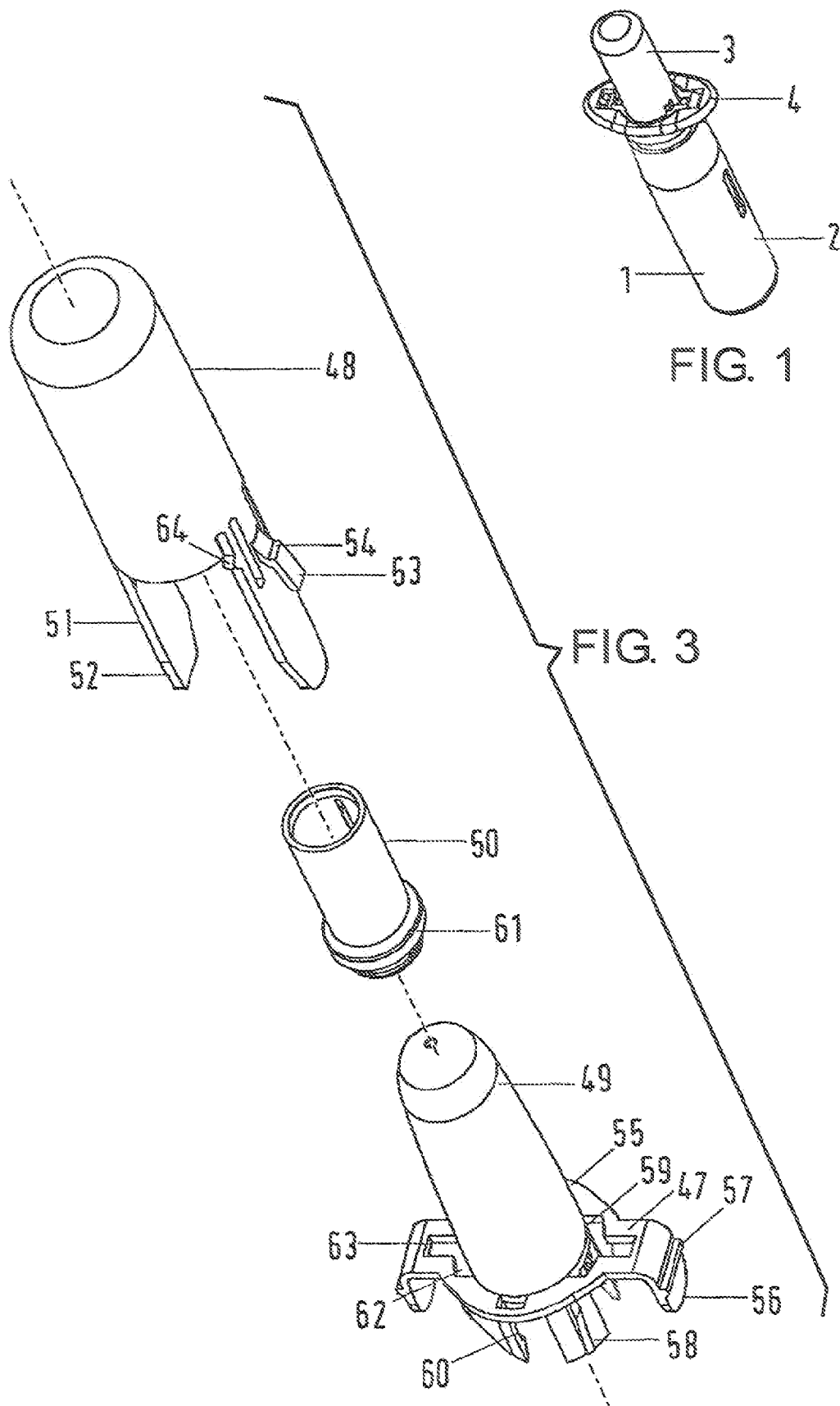
FIG. 1 is a perspective view of a device for dispensing a pharmaceutical substance in accordance with a first embodiment of the invention.

The perspective view of FIG. 1 shows a device 1 for dispensing a pharmaceutical substance. The device includes a main body 2 and a unit 3 mounted on the main body, this unit containing the pharmaceutical substance to be dispensed. In this embodiment, where the pharmaceutical substance is intended for nasal administration, the unit 3 has dimensions appropriate for insertion into the user's nasal cavity, after removal of a protective cover. In view of its shape and function, the unit 3 which contains the pharmaceutical substance is referred to in the following description as a nozzle unit.

The main body 2 is of a generally cylindrical configuration and includes a flange forming a pair of shoulders 4 at its upper end. The device is intended to be held by the user with the nozzle unit between two fingers, which thus rest on the shoulders, and the thumb on the bottom part of the main body, the nozzle being placed in the nasal cavity.

Figure 2:
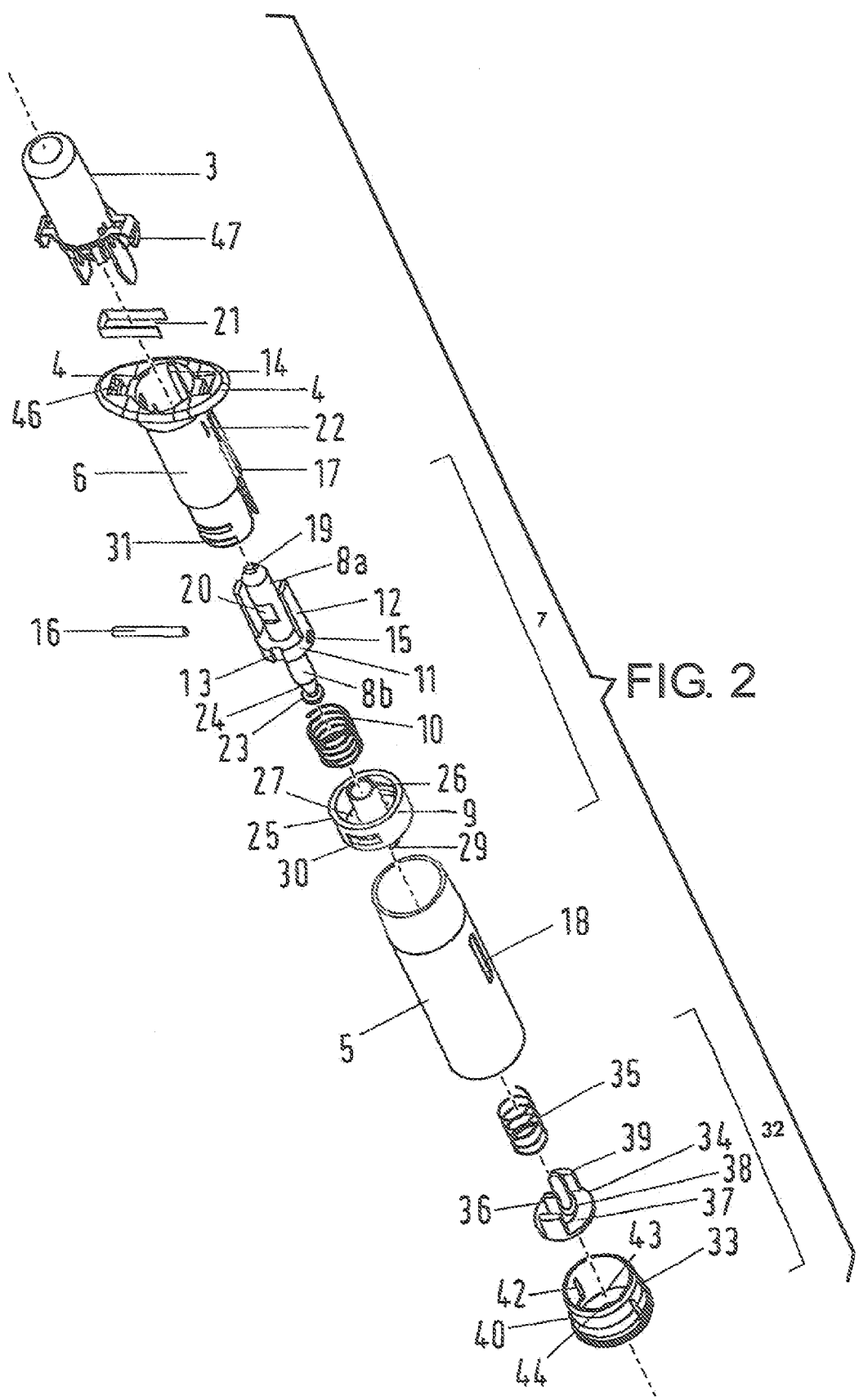
FIG. 2 is an exploded perspective view of the device of FIG. 1.

In the exploded perspective view of FIG. 2 the nozzle unit 3 is shown at the upper part of the figure, separated from the main body 2. The main body 2 includes a cylinder 5 and a sleeve 6 which can be slidably located within the cylinder 5. The shoulders 4 are formed at the outer end of the sleeve 6.

Between the sleeve 6 and the cylinder 5 is shown a plunger assembly 7. This assembly comprises a pusher rod 8 and a retention clip 9, these parts being urged away from each other by a spring 10.

The pusher rod 8 has an annular rim 11 midway along its length with upper rod portion 8a extending above the annular rim 11 and lower rod portion 8b extending below the rim 11. On diametrically opposite sides of the rim 11 legs 12 extend upwardly, parallel to the axis of the rod 8. The length of the legs 12 is less then that of the upper rod portion 8a.

The rim 11 includes a recess 13 on diametrically opposite sides thereof, between the legs 12, for receiving an inner longitudinal rib 14 of the sleeve 6. The location of the ribs 14 in the recesses 13 prevents relative rotational movement of the pusher rod 8 within the sleeve 6.

The rim 11 also has a transverse bore 15 for a pin 16. Longitudinal slots 17 in the sleeve 6 and slots 18 in the cylinder 5 accommodate longitudinal movement of the ends of the pin 16.

The upper portion 8a has a rounded head 19 and two diametrically opposing segmental recesses 20 along its length for receiving the arms of a U-shaped clip spring 21. The clip spring 21 is fitted in the sleeve 6 by means of a pair of small slots 22 on each side of the sleeve. The clip spring 21 is pushed into the sleeve from one side, through a first pair of the slots 22, and the ends of the arms of the spring are then located in the second pair of slots 22 (visible in FIG. 2). The arms of the spring 21 thus extend across the hollow interior of the sleeve 5. A shallow recess (not seen) between the first pair of slots 22 in the sleeve accommodates the base of the U-shaped clip. The clip 21 is firmly secured in place by virtue of the subsequent location of the sleeve 6 in the cylinder 5.

The lower rod portion 8b has a head 23 which is separated from the remainder of the portion 8b by a narrower neck portion 24.

The retention clip 9 comprises an outer cylindrical portion 25 and an inner cylindrical portion 26, joined by an annular floor portion 27. The floor portion 27 defines a seat for one end of the spring 10, the other end being seated against the lower surface of the rim 11 of the pusher rod 8.

The lower end of the cylindrical potion 26, below the floor 27 has longitudinal slots thus forming clip arms 29. The inner cylidrical potion 26 is for receiving the lower portion 8b of the pusher rod 8, the head 23 of the lower potion 8b being able to clip over the ends of the clip arms 29 of the retention clip 9.

The outer cylindrical portion 25 of the retention clip 9 has a pair of circumferential recesses 30 for receiving one of a pair of ribs 31 at the lower end of the sleeve 6. Thus, the retention clip 9 can be mounted on the end of the sleeve 6 with the pusher rod 8 and spring 10 inside. Before connection of the retention clip 9 on the sleeve 6, the sleeve is inserted into the upper end of the cylinder 5 and the pusher rod and spring are inserted from the lower end of the cylinder, the retention clip then also being pushed in the lower end of the cylinder and clipping over the bottom of the sleeve 6.

The main body 2 also includes a resilient trigger device 32 comprising a cap 33 defining a seat for an actuating button 34, together with a buttonspring 35. The actuating button 34 comprises an inner pair of arms 36 which locate within the slots between the clip arms 29 of the retention clip 9. The spring 35 is held between an annular floor 37 of the actuating button 34 and the lower surface of the floor 27 of the retention clip 9. At the end of the arms 36 nearest to the floor 37 there is an inclined portion 38; in other words, each arm 36 flares as it approaches the floor 37. This flared portion of each arm 36 will tend to separate the clip arms 29 of the retention clip 9, when pushed into the respective slot 28 of the retention clip.

The button 34 also has an outer pair of arms 39 which assist proper location of the button within the cap 33.

The cap 33 for the trigger device 32 clips inside the cylinder 5, an annular rim 40 on the cap locating in a correspondingly shaped annular recess 41 (FIG. 4) on the inside of the lower end of the cylinder. A sufficient degree of resiliency to the rim 40 so as to allow insertion of the cap into the cylinder is provided by slots 42 in the cap 33.

The cap 33 has an annular floor 43 with a central aperture 44. The aperture 40 receives the button nub 45 (not seen in FIG. 2) which extends below the floor 37 of the button 34.

Each shoulder 4 of the sleeve 6 has an aperture 46 for receiving a wing portion 47 of the nozzle unit 3. This nozzle unit 3 is shown in more detail in the exploded perspective view of FIG. 3. The nozzle unit 3 includes a cap 48, a nozzle member 49 and a vial holder 50 which holds a vial of the pharmaceutical substance to be dispensed (the vial not being visible in this Figure). Extending downwards from each side of the cap 48 are cap legs 51 with tapered ends 52. The cap also has a resilient cap wing 53 extending outwardly and downwardly therefrom, approximately at the base of the cap legs 51. The cap wing 53 includes a shoulder 54.

The nozzle member 49 has a laterally extending skirt 55 at opposite sides of which are formed the skirt wings 47. Each wing 47 has a resilient portion 56 which extends downwardly, i.e. perpendicular to the plane of the skirt 55. These portions 56 include transverse lips 57 which positively engage underneath the shoulders 4 of the sleeve 6 upon mounting of the nozzle unit 3 on the device 1, with the portions 56 entering the apertures 46 of the shoulders of the sleeve 6.

The skirt 55 has depending skirt legs 58 and skirt openings 59 on either side of the nozzle. The skirt legs 58 include, on their inner surface, a circumferential groove 60. The vial holder 50 is of a generally cylindrical shape and locates within the nozzle member 49, a circumferential rim 61 at the base of the vial holder locating in the circumferential groove 60 of the skirt legs 58 to hold the vial holder securely within the nozzle member. The skirt legs 58 have a degree of resiliency so that the vial holder can be pushed further within the nozzle member 49 by an appropriate force.

Each skirt opening 59 of the skirt 55 has an inner, wider portion 62 and a narrower, outer portion 63. The inner wider portions 62 are for receiving the cap legs 51. The narrower outer portions 63 are for receiving the cap wing 53. The cap legs 51 include a small rounded protrusion 64 at their base, this protrusion clipping behind the skirt 55 upon mounting of the cap 48 on the nozzle member. It can be noted at this point that when the cap is mounted on the nozzle member there is a spacing between the underside of the skirt 55 and the shoulder 54 of the cap wing 53.

The inner construction and the working of the nozzle member is, in this embodiment, exactly as described in European patent application number EP-A-0546607. Thus the way in which the pharmaceutical substance is held within the nozzle member, and the way in which it is dispensed, need not be described in detail here. It can, however, be noted that the vial holder 50 in the present device is shorter than the equivalent member in EP-A-0546607. In the present case, it can be seen that the vial holder does not extend beyond the ends of the skirt legs 58, so that accidental pressure on the vial holder 50, when the nozzle units are handled by the user, is avoided, the skirt legs 58 surrounding and protecting the vial holder 50.

As already indicated, the nozzle units 3 are intended for one use only and will thus be disposed of after use. The user will have a supply of nozzle units and the actuating device may be stored in a carry-case along with a small supply of spare nozzle units.

Figure 4:
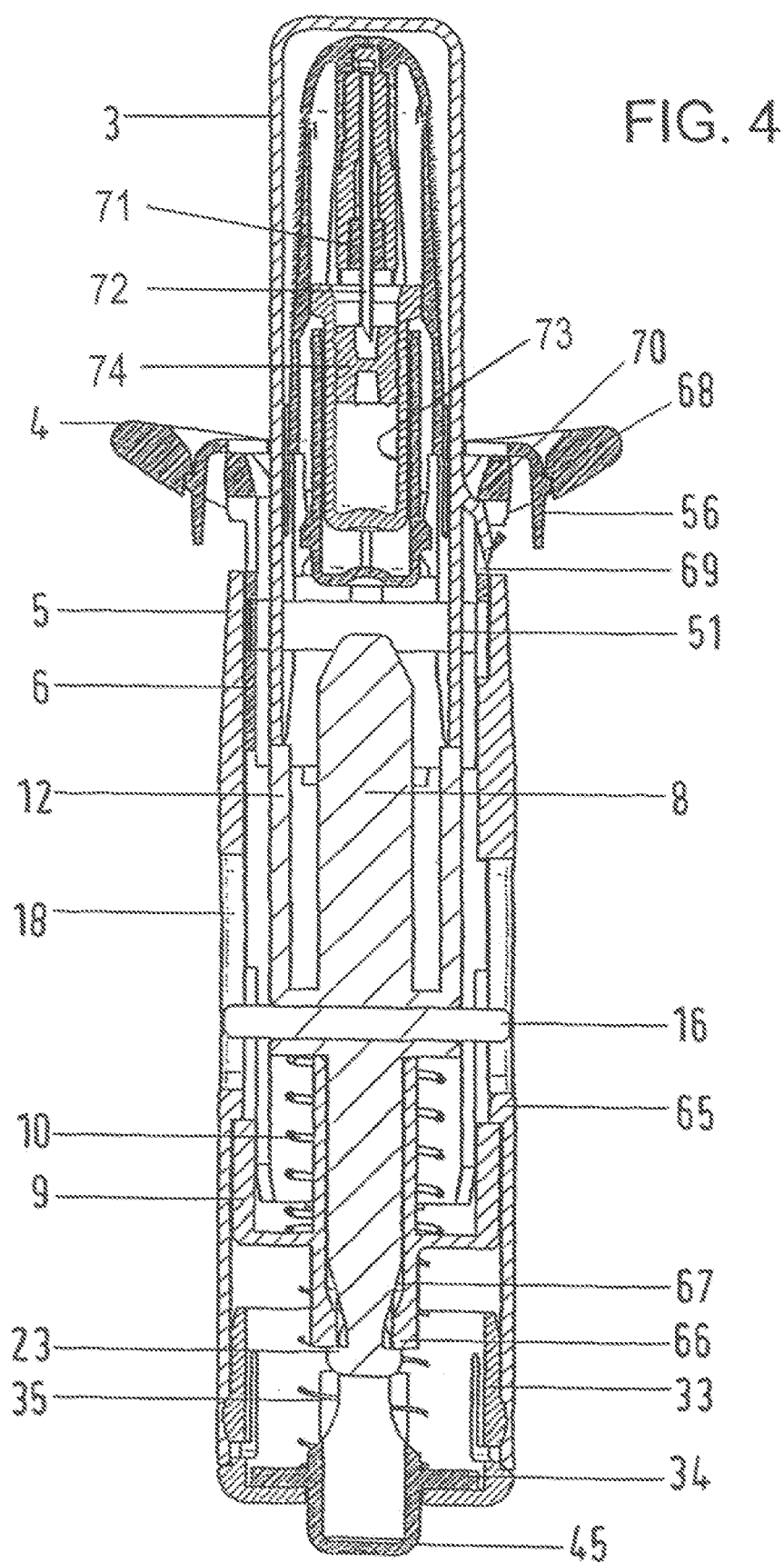
FIG. 4 is a longitudinal sectional view of the device, showing the unit containing the pharmaceutical substance in its mounted condition.

The sectional view of FIG. 4 shows the actuating device 1 with a new nozzle unit 3 mounted thereon. The Figure also shows all of the component parts of the device, shown separated in FIG. 2, in their normal assembled condition. To achieve this condition, the pusher rod 8 and the sleeve 6, with the clip spring 21 in position, are placed in the cylinder 5 from above and the spring 10 and retention clip 9 are placed in the cylinder from below, the retention clip engaging with the end of the sleeve. The retention clip 9 is prevented from moving along inside the cylinder 5 by means of an internal shoulder 65 of the cylinder. The cap spring 35, the cap button 34 and the cap 33 are then pushed onto the end of the cylinder. Finally, the pin 16 is pressed fitted into the pin bore 15 of the pusher rod 8. The length of the pin 16 is the same as the diameter of the cylinder 5 so that the ends of the pin can travel along the slots 17 and 18 of the sleeve 6 and cylinder 5 respectively.

In the initially assembled state of the pusher rod 8 within the sleeve 6 and cylinder 5, the pusher rod 8 is at an advanced position within the sleeve. In particular, the rod is held in this advanced position by means of the clip spring 21 which locates in the recesses 20 of the pusher rod. In this condition, the main spring 10 is relaxed and the head 23 of the pusher rod 8 is slidably located inside the inner cylindrical portion 26 of the retention ring 9. To compress the main spring 10 and thus to prime the pusher rod 9, the pusher rod must be retracted—i.e. moved downwardly—so that the head 23 of the pusher rod is located over the ends of the arms 29 of the retention ring 9, as shown in FIG. 4. This Figure illustrates that the arms 29 have thickened portions 66 at the ends with an inner inclined surface 67, so that when the pusher rod 8 is pushed downwardly the head 23 will force apart the arms 29 and then the thickened portions 66 will locate in the neck 24 of the rod 8, behind the head 23.

To move the pusher rod to this retracted position, the nozzle unit 3 shown in FIG. 3 is mounted on the end of the device so that the legs 51 slide inside the sleeve 6 and the wings 47 locate in the apertures 41 of the shoulders 4. Mounting of the nozzle unit 3 has a number of effects. As the legs 51 of the cap 48, which is fitted on the nozzle member 49, travel inside the sleeve 6, the tapered portions 52 of the legs 51 open the arms of the clip spring 21 so that the clip spring 21 is released from the recesses 20 of the pusher rod 8. The pusher rod 8 is thus freed for movement within the sleeve 6. Also, as the nozzle unit 3 continues to be pushed onto the sleeve 6, the legs 51 travel within the sleeve until the ends of the legs 51 abut the ends of the legs 12 of the pusher rod 8. Via the contact between the legs 51 and the legs 12, mounting of the nozzle unit 3 on the sleeve 6 thus has the effect of pushing the pusher rod 8 into a retracted position within the sleeve with the head 23 of the pusher rod held over the ends of the arms 29 of the retention ring 9.

This position is shown in FIG. 4 which also shows the pin 16 at a relatively rearward position along the slot 18 of the cylinder 5. At the point at which the head 23 of the pusher rod is located over the arms of the retention ring, the wings 47 of the nozzle member 44 are also fully located in the openings 46 of the shoulders 4, with the lips 57 of the skirt wings located underneath a shoulder 68 on the inside of the openings 46. Furthermore, the cap wing 53 locates in an aperture 69 on the inside of the upper end of the sleeve 6, the wing 53 having been retracted by the inclined sides of the mouth of the sleeve 6. It can be noted that the wing 53 extends sufficiently laterally of the sleeve 6 such that it is adjacent the upper end of the cylinder 5. The shoulder 54 of the wing 53 is firmly located under an edge 70 of the shoulder 4. It will thus be understood that the presence of the wing 53 prevents upward sliding movement of the cylinder on the sleeve and thus any sliding movement of the sleeve into the cylinder. If desired, a wing 53 can be provided on both cap legs 51.

In the sectional view of FIG. 4 are also seen the internal component parts of the nozzle unit 3. As described in more detail in EP-A-0546607 there is a piston member 71 in which is mounted a hollow needle 72. Held within the vial holder 43 is a vial 73 closed by a rubber stopper 74. The hollow needle 72 is in alignment with the opening of the nozzle. Upon depression of the vial holder 43, the needle 72 pierces the rubber stopper 74 and the stopper is pushed along the vial 73 by the piston member 71, thus expelling all of the contents through the needle and thus through the nozzle opening.

Figure 5:
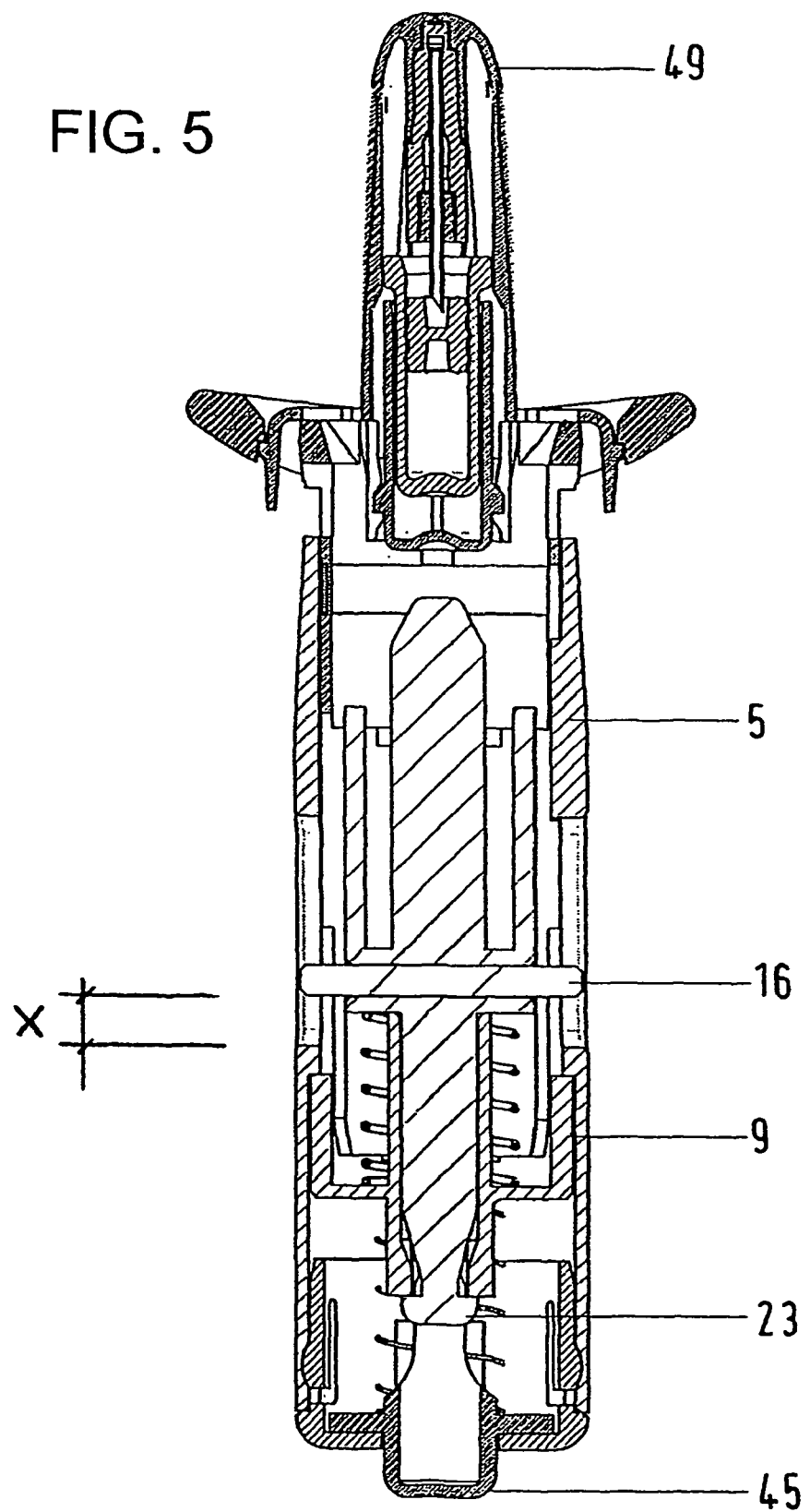
FIG. 5 is a sectional view similar to that of FIG. 4, but showing the unit containing the pharmaceutical substance with its cap removed, ready-to-use.

The next stage in the actuation of the device is the removal of the cap 48. The cap is simply removed by the user pulling it off the shoulders 4. The force required to remove the cap is not great, as only disengagement of the rounded protrusion 64 on the legs 51 and disengagement of the shoulder 54 of the resilient cap wing 53 is required. The condition of the device with the cap removed is shown in FIG. 5. The device is now ready for actuation by the user. As previously mentioned, the device will be held between the user's fingers and thumb, with the nozzle member inserted in the user's nasal cavity. Upon pressing of the button of the user's thumb two movements will occur. Firstly, the sleeve 6 will slide further into the cylinder 5, being no longer blocked by the cap wing 53, the extent of this movement shown by the distance X in FIG. 5, which also is the distance the indicator pin 16 can travel to the end of the slot 18. The other movement is the depression of the button member 34 by the user's thumb, against the action of button spring 35. It will be appreciated that button spring 35 has already been depressed by the movement of the sleeve 6 within the cylinder 5, as with this movement retention ring 9, against which the button spring is seated, moves with the cylinder 5.

Movement of the retention clip 9 towards the button member, as the sleeve 6 is pushed into the cylinder 5, and then movement of the button member 34 towards the retention ring 9 by depression of the button, causes the arms 36 of the button to move along the slots 27 between the arms 26 of the retention clip 9 sufficiently far that the flared portions 38 of the button arms are forced into the slots 28 of the retention clip, thereby separating the arms 29 of the retention clip 9.

It should be emphasized at this point that depression of the button 34, without movement of the sleeve 6, would not be sufficient to move the flared portions 38 of the button into the slots 29. Conversely, movement of the sleeve 6 into the cylinder 5 without depression of the button 34, is insufficient to force the flared portions into the slots 29 as the travel of the sleeve 6 is restricted by the geometry of the device (the permitted travel of the indicator pin 16, the permitted travel of the retention clip 9 towards the cap 40 and the permitted travel of the shoulders 4 before they abut the end of the cylinder 5).

Figure 6:
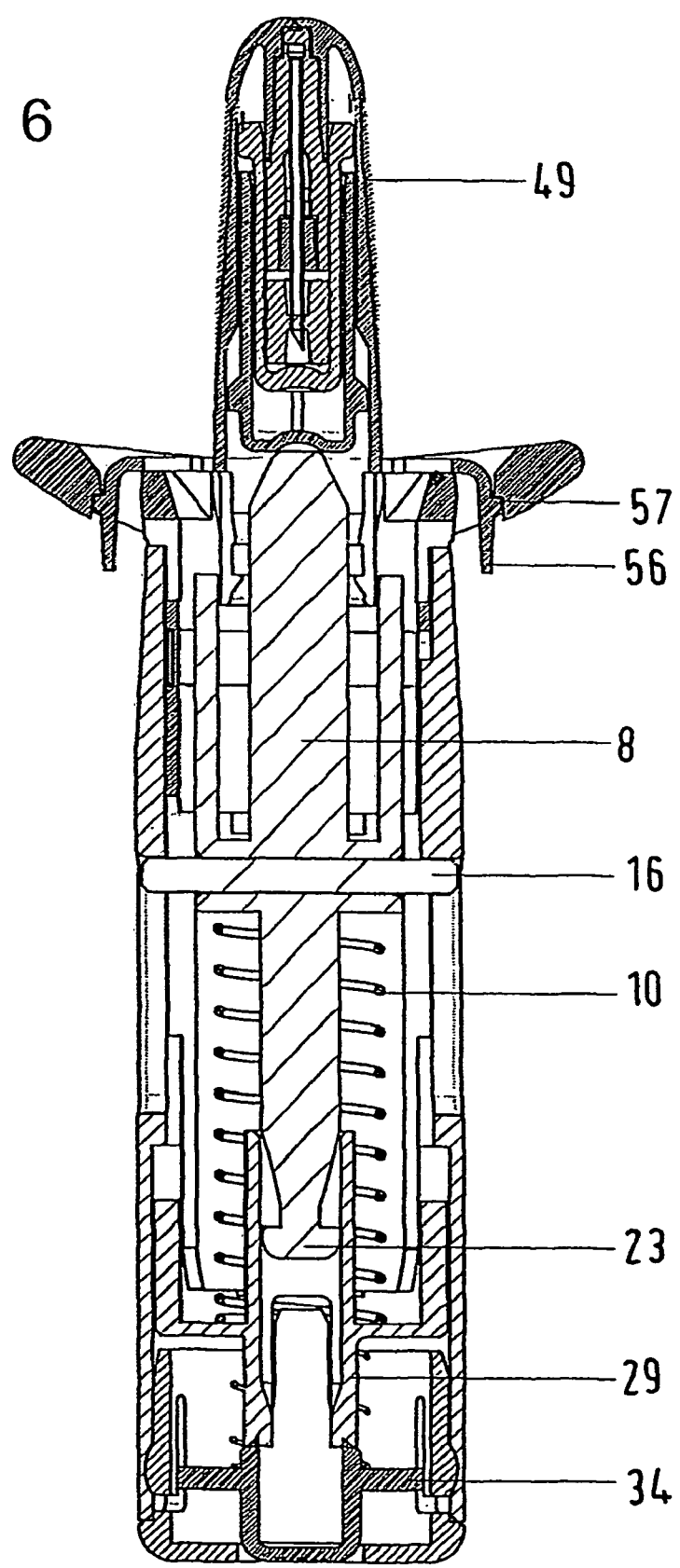
FIG. 6 is a similar sectional view, showing the device in an actuated condition.

As indicated in FIG. 6, the separation of the arms of the retention clip releases the head of the pusher rod and the pusher rod is therefore moved upwardly by the force of the main spring 10. The rounded end 19 of the pusher rod engages the bottom of the vial holder 50 and then pushes the vial holder into the nozzle member 49, this in turn forcing the needle to penetrate the stopper and the vial to travel over the piston member, in the same way as described in relation to EP-A-0546607. The pusher rod is now in an advanced position and the clip spring 21 again locates in the recess 20 of the pusher rod. Also, the indicator pin is at the upper end of the slot 18. It will be appreciated that the position of the pin 16 acts to display clearly the condition of the device. The forward position shown in FIG. 6 indicates that the device has been discharged and the pusher rod is not primed (i.e. the main spring is not compressed). On the other hand, the position of the pin as seen in FIGS. 4 and 5, further down the slot, indicates that the device is ready-to-use with the pusher rod primed and the main spring compressed.

After actuation of the device, the used nozzle member 49 will need to be disposed of. To remove the nozzle member from the shoulders 4 of the sleeve 6, the ends of the skirt wing portion 56, below the shoulders, are squeezed inwardly by the user's finger and thumb, thus releasing the lips 57 of the skirt wings 47 from the internal shoulder 68 of the shoulder 4. The cylinder and sleeve assembly, without any nozzle unit attached, can now be replaced in the carry-case (not shown) ready for use with a new nozzle unit.

While the operation of the device has to some extent been described in relation to FIGS. 1 to 6, for completeness the use of the device will be briefly explained again. If it is assumed that the pharmaceutical substance contained in the nozzle unit is Sumatriptan, then the device will be used for the alleviation of the symptoms of a migraine. On sensing the onset of a migraine attack, the user will open the carry-case and remove the cover and sleeve assembly and one nozzle unit. The nozzle unit is then mounted on the cylinder and sleeve assembly until the skirt wings have engaged on the shoulders of the sleeve, the legs of the cap thus pushing in the pusher rod until its head has engaged over the ends of the arms of the retention clip. The indicator pin, in its lower position, will show the user that the device is primed, ready for use. The cap is pulled off and the device placed in position, in the user's nasal cavity. Compression of the device between the user's fingers and thumb both moves the sleeve into the cylinder and depresses the button, the arms of the button thus opening the arms of retention clip to release the piston rod which, under the force of the main spring, drives the vial holder into the nozzle member to dispense the substance from the vial through the nozzle opening. The used nozzle member is removed and disposed of. It is thus understood that the device is easy to use and can be operated in a reliable and straightforward fashion to quickly and efficiently dispense a dose of pharmaceutical substance, as the need arises.

It will also be appreciated that the device includes several security features to ensure that the device is operated in the intended fashion. In particular, the following features are included.

1. The legs of the cap are required for the device to be primed. Thus, only a nozzle unit with a protective cap in place can be mounted on the device to prime it. Once the cap has been removed from the nozzle member it cannot be easily refitted. Thus, there is little or no possibility of the device being used in combination with a nozzle member which has previously been used.
2. The device cannot be primed by forcing a pen or the like into the sleeve, or by pulling back the indicator pin, because of the blocking action of the clip spring.
3. Until the cap is removed, movement of the sleeve within the cylinder is blocked by the cap wing. Thus, there is no possibility of the device being discharged with the cap in place. The chance of inadvertent actuation of the device, before the nozzle member is correctly placed in the nasal cavity, is thus very limited.
4. The indicator pin always shows the user the actuation state of the device.

FIGS. 7 to 12 show a second embodiment of the dispensing device. In essence, the second embodiment is a fully manual version of the device shown in FIGS. 1 to 6, that is the discharge of the pharmaceutical substance occurs by means of manual pressure (more precisely the pressure of the user's thumb) rather than spring force. As will become apparent from the following description, in the manual version there is no requirement for a sliding cylinder/sleeve assembly or for the retention clip and button assemblies by which the main spring of the first embodiment is compressed and then released.

The elevational view of FIG. 7 shows the dispensing device 101 which includes a main body 102 and a unit 103 mounted on the main body, this unit containing the pharmaceutical substance to be dispensed. In this embodiment, like in the first embodiment, the unit 3 has dimensions appropriate for insertion into the user's nasal cavity, after removal of the protective cover. The unit will be referred to below as a nozzle unit.

The main body 102 is of a generally cylindrical configuration and includes a rim 104 at its upper end. The rim is, in plan view, generally oval shaped and so extends outwardly on two sides to form shoulders. In use, the shoulders will support two fingers of the user's hand, the is user's thumb then being placed on the bottom part of the main body, with the nozzle being placed in the nasal cavity.

In the exploded view of FIG. 8 the nozzle unit 103 is shown at the upper part of the Figure with its component parts shown separately. These will be described in more detail below. The main body 102 is shown at the lower part of the Figure and includes a cylinder 105 and a sleeve 106 which can be fitted around the cylinder 105, below the rim 104. The main body 102 also includes a generally cylindrical, elongate pusher rod 108, an annular retention ring 109 and a spring 110.

The pusher rod 108 is divided into three portions 108a, 108b and 108c. Portion 108c is at the lower end and is separated from portions 108b and 108a by annular rim 111. Portion 108a is at the upper end and is separated from portion 108b by an inclined shoulder 112. The diameter of pusher rod portion 108b is thus greater than the diameter of pusher rod portion 108a. The diameter of pusher rod portion 108c is greater than that of portion 108a, but less than that of portion 108b.

Spring 110 is mounted around portion 108*b* and between the retention ring 109 and the annular rim 110. Thus, the spring 110 acts to urge the pusher rod 108 away from the retention ring 109. On assembly of the pusher rod 108 within the cylinder 105, pusher rod portion 108*c* extends out of a central aperture 113 (not seen in FIG. 8) at the bottom of the cylinder 105.

At the opposite end of pusher rod 108 to the portion 108*c* is head portion 119. Immediately below the head portion 119 there is an annular groove 120*a* which can receive the arms of a U-shaped clip spring 121*a*. Similarly, below the inclined shoulder 112 of the pusher rod 108 there is a second annular groove 120*b* which can receive the arms of a second U-shaped clip spring 121*b*. The clip springs 121*a* and 121*b* are fitted into the cylinder 105 by means of slots 122, the arms of the clip springs thus extending across the hollow interior of the cylinder. After mounting of the clip springs on the cylinder, the sleeve 106 can be forced over the cylinder 105 to keep the clip springs in position.

The rim 104 of the cylinder 105 includes a peripheral lip 123 which defines a seat for the nozzle unit 103. The rim 104 also has apertures 124 on opposite sides of the mouth of the cylinder.

The nozzle unit 103 includes a protective cap 148, a nozzle member 149 and a vial holder 150 which holds a vial of the pharmaceutical substance to be dispensed. Extending downwardly from each side of the cap 148 are cap legs 151 with tapered ends 152. The cap legs 151 themselves have intermediate cap wings 153. At the upper end of the cap legs 151, immediately before they join the cap part, there are protrusions 164.

The nozzle member 149 has a laterally extending skirt 105 which in plan view has an oval shape. The skirt can locate within the peripheral lip 123 of the rim 104 of the cylinder 105. The skirt includes downwardly extending wings 156 which can locate in the apertures 124 of the rim 104. The wings 156 each have a transversely extending lip 157 (not visible in FIG. 8). As in the first embodiment, the skirt includes skirt legs 158 in which the vial holder 150 is fitted. Further description of the interior of the nozzle member 149 will not be given, as it is the same as that of the device of FIG. 1. Skirt openings 159 are for receiving the legs 151 of the protective cap 148, when it is fitted on the nozzle member 149.

Each nozzle unit contains a unit dose of the pharmaceutical substance and is intended for one use only; each unit will thus be disposed of after use. The user will have the supply of nozzle units and the actuating device may be stored in a carry case with a small supply of nozzle units.

Figure 9:
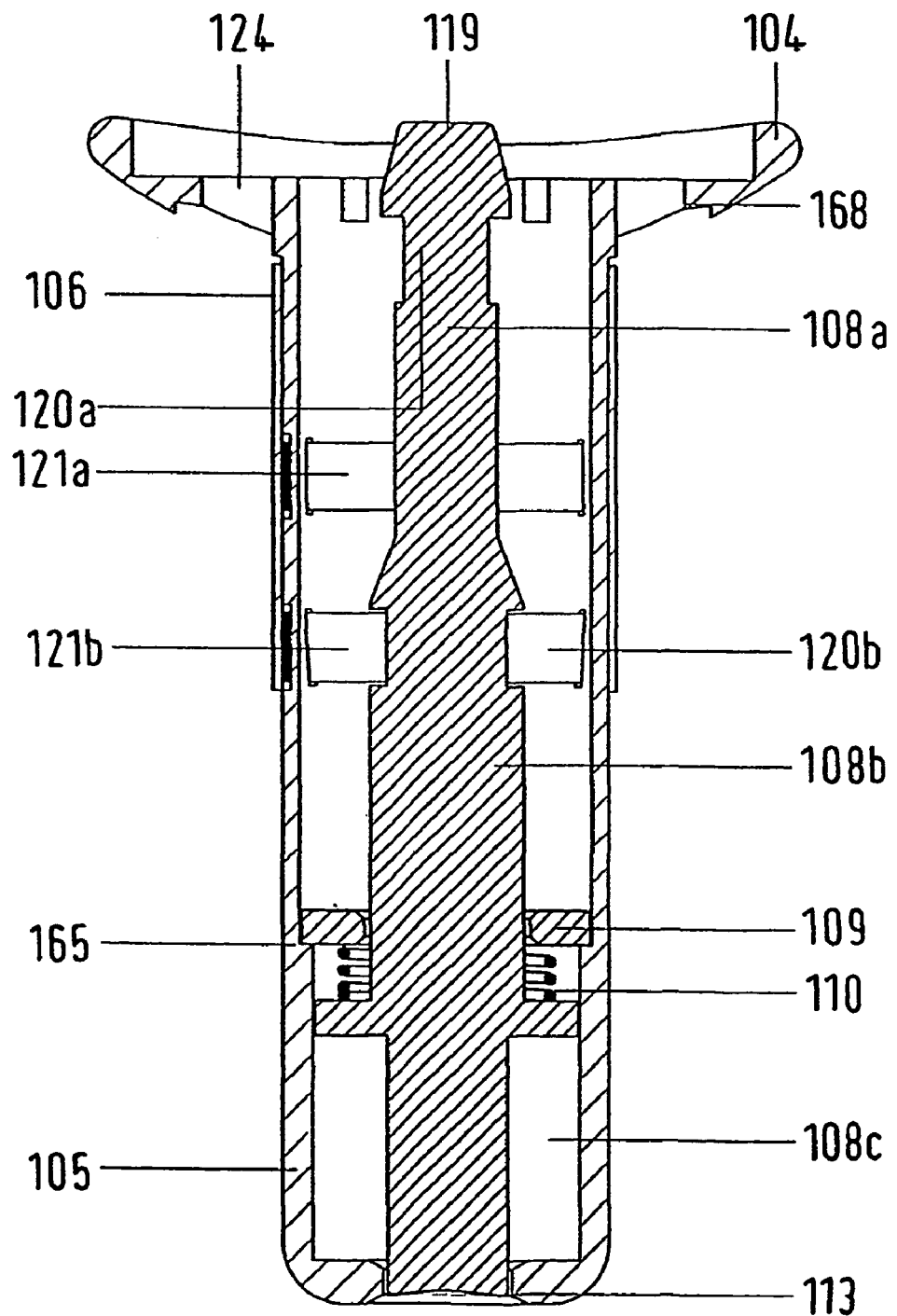
FIG. 9 is a longitudinal sectional view of the device, before mounting of the unit containing the pharmaceutical substance.

The sectional view of FIG. 9 shows the pusher rod 108 mounted within the cylinder 105. The pusher rod is in its "dormant" position, i.e. the position it assumes before a nozzle unit is mounted on the cylinder 105 (which is also the position it assumes after actuation of the device and removal of the used nozzle unit). In this position, the head 119 of the pusher rod 118 is approximately at the level of the rim 104 of the cylinder 105. The end of pusher rod portion 108*c* locates in the central aperture 113 of the lower end of the cylinder 105. It will be appreciated that the length of the pusher rod 108 is approximately the same as that of the cylinder 105 and so in the dormant position of the pusher rod 108 it does not protrude from either end of the cylinder 105.

FIG. 9 also shows the retention ring 109 fitted in position within the cylinder 105. Retention ring 109 abuts a shoulder 165 within the cylinder 105 and is fixed in this position, for example by force fitting within the cylinder. The spring 110 is shown between the retention ring 109 and the rim 111 of the pusher rod 108. In the dormant position of the pusher rod 108 the spring 110 is compressed.

The pusher rod 108 is maintained in the position seen in FIG. 9 by means of the travel spring 121*b* which locates in the annular recess 120*b* of the pusher rod 108. The other clip spring 121*a* is positioned above the clip spring 121*b* and thus encloses the pusher rod portion 108*a*. As this portion is relatively narrow, in this position of the pusher rod 108 the clip spring 121*a* has no effect. Annular recess 120*a* is in turn above the position of clip spring 121*a*.

In the sectional view of FIG. 9 can clearly be seen the apertures 124 of the rim of 104, together with an internal shoulder 168 under which the lips. 157 of the nozzle unit can engage.

Figure 10A:
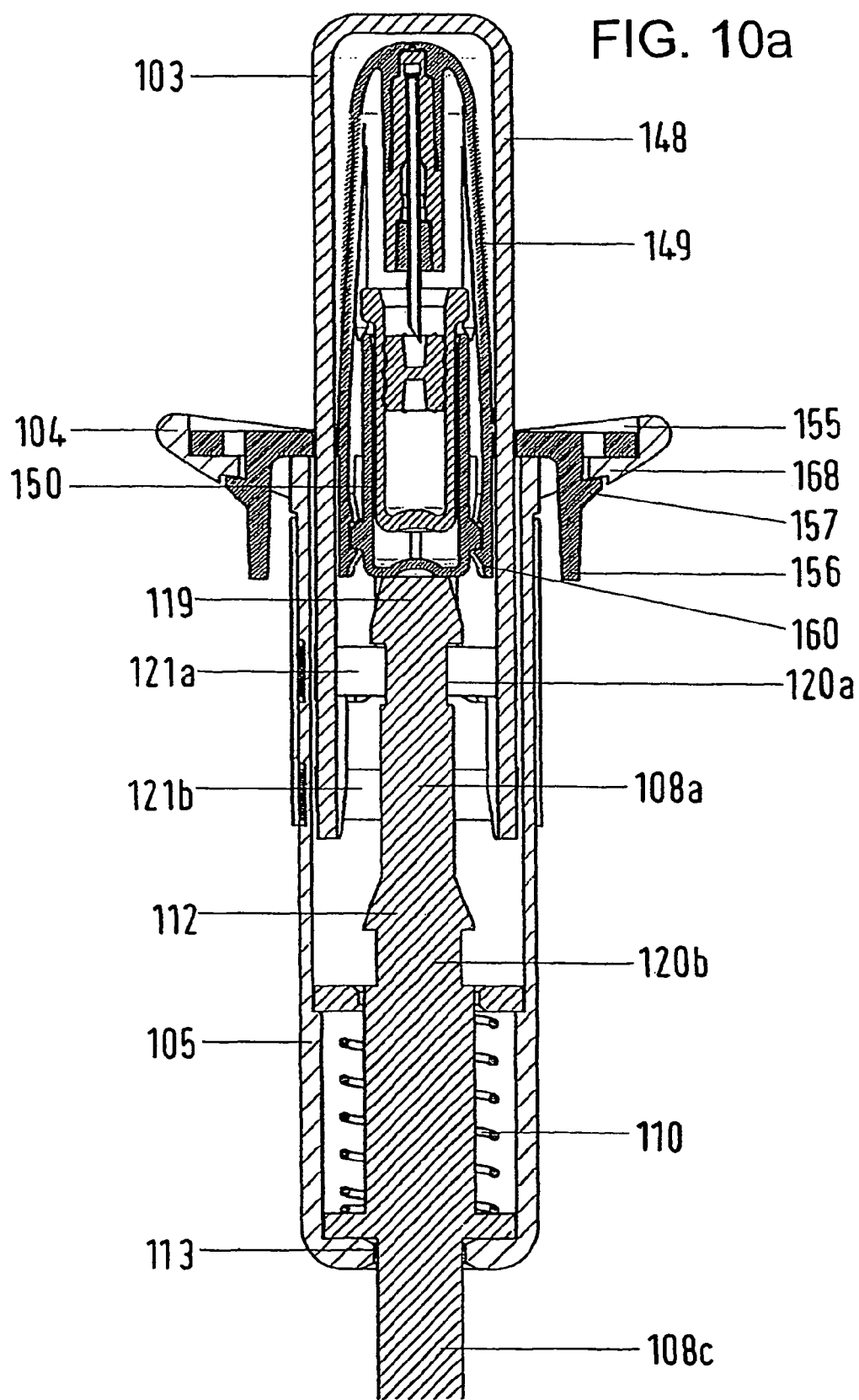

The sectional view of FIG. 10*a* shows the cylinder 105 with the nozzle unit 103 mounted thereon. As will be described with reference to FIG. 10*b*, mounting of the nozzle unit 103 moves the pusher rod 108 from its dormant position to its actuation position in which portion 108*c* extends out of the opening 113 of the cylinder 105. This movement is limited by the annular rim 111 abutting the end of the cylinder 105. Pusher rod 108 is able to adopt this position by virtue of the release of clip spring 121*b* from the annular recess 120*b*. Upon release of the clip spring 121*b*, the spring 110 forces the pusher rod 108 in a downward direction.

The nozzle unit 103 is pushed onto the cylinder 105 until the lips 157 positively engage under the shoulders 168 of the rim 104. This action is aided by the resilience of the wings 156 and the inclined lower surfaces of the lips 157. In the fully mounted position of the nozzle unit 103, the vial holder 150 is immediately adjacent the head 119 of the pusher rod 108. Furthermore, the pusher rod 108 is in such a position that the arms of the clip spring 121*a* locate in the annular recess 120*a* of the pusher rod, the clip spring 121*b* now being in an inactive position around the narrow portion 108*a* of the pusher rod. With clip spring 121*a* located in the annular recess 120*a*, the pusher rod 108 is blocked in the actuation position, with its lower portion 108*a* extending out of the cylinder 105.

FIG. 10*b* indicates the cooperation between the cap legs 151 and wings 153 and the clip springs 121*a* and 121*b*, and shows the cap 148 above a section of the pusher rod 108 which has been isolated and enlarged for clarity. The width of the cap leg 151 is such that it can pass through the arms of clip spring 121*a*. The arms of clip spring 121*b* are, however, inclined so that they present a narrowed opening to the tapered end of the cap leg 151. Thus, the leg 151 will open clip spring 121*b* in order to release that spring from the recess 120*b* of the pusher rod 108. Upon further downward movement of the cap 148, the inside surfaces of the cap wings 153 will close the clip spring 121*a*, into the recess 120*a*.

The opposite spring actions occur upon removal of the cap 148. Thus, when the cap wings 153 are pulled away from the clip spring 121*a*, it opens to disengage from the recess 120*a*. Similarly, when the cap legs 151 are no longer between the arms of the clip spring 121*b*, it can move to its closed position.

Figure 11:
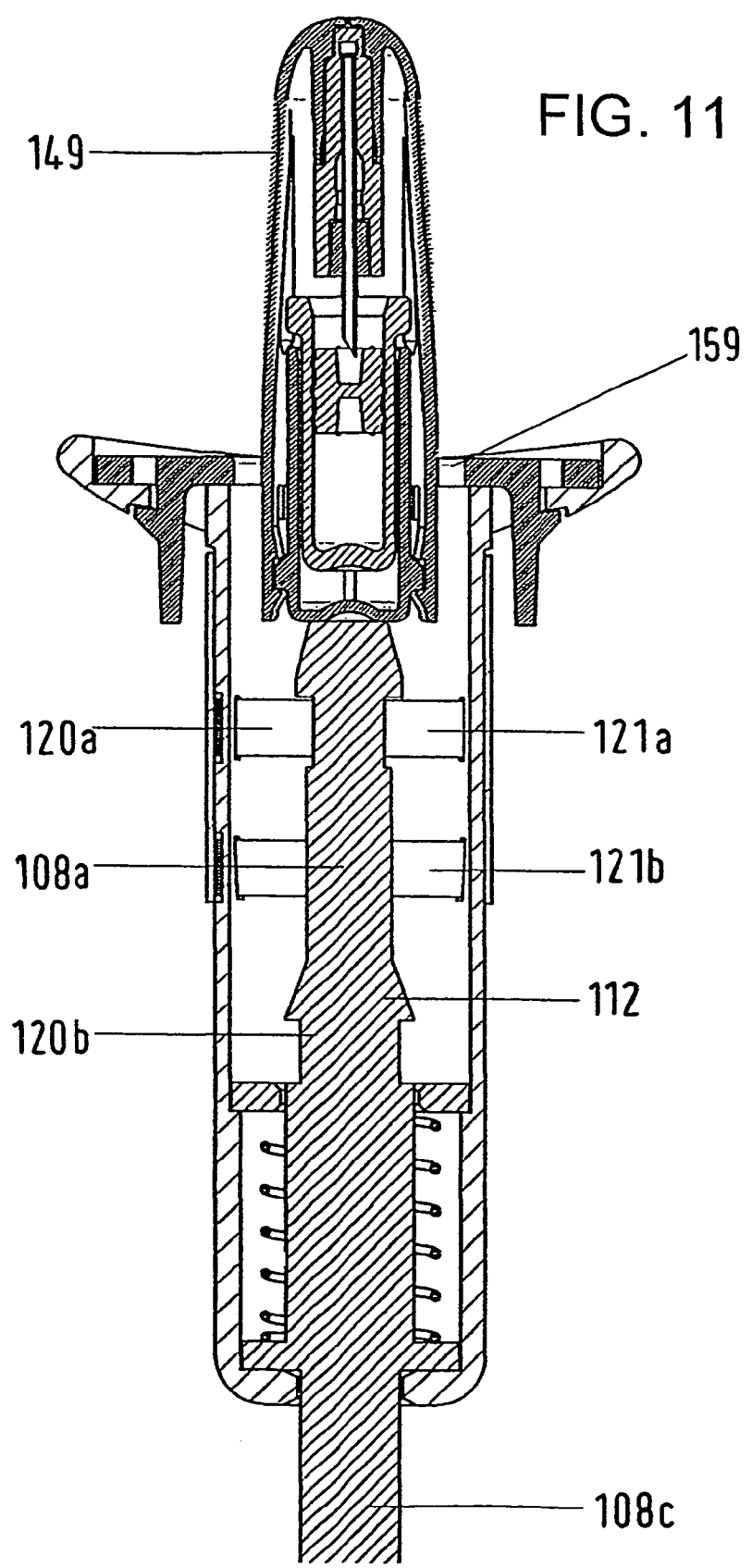
FIG. 11 is a similar sectional view to that of FIG. 10a, showing the device with the cap removed, ready-to-use.

It can be mentioned at this point that the shape of the protrusions 164 on the cap legs 151 is such that removal of the cap 148 from the nozzle member 149 is relatively easy, but re-fitting is very difficult. Specifically, the protrusions 164 present an inclined surface when they address the nozzle skirt 155 from below, but a flat surface when they address the skirt 155 from above. Compression of the cap wings 151 is possible due to the presence of slits adjacent the protrusions 164. The cap 148 is fitted to the nozzle member 149 during manufacture, by mechanical squeezing of the legs to allow the protrusions 164 to pass through the skirt openings 159. FIG. 11 shows the dispensing device with the protective cap 148 removed from the nozzle unit 103. As previously mentioned, to remove the cap 148 it simply needs to be pulled off by the user, a relatively low force being required to disengage the protrusions 164 from the nozzle skirt 155. After this disengagement, the cap legs 151 are pulled out through the skirt openings 159. The removal of the cap 148 does not affect the position of the pusher rod 108. However, as described above in connection with FIG. 10b removal of the cap has the effect of opening the clip spring 121a so that it is no longer engaged in the annular groove 120a of the pusher rod. In other words, the pusher rod 108 is no longer blocked by the clip spring 121a.

As mentioned in relation to FIG. 10a, the other clip spring 121b is located at the narrow portion 108a of the pusher rod, so that it too is not blocking the pusher rod. The device is now in the condition in which the pusher rod is free to move within the cylinder, against the action of the spring 110. By pressing the pusher rod portion 108c, into the cylinder 105, the user will force the head 119 of the pusher rod against the vial holder 150 and then dispense the contents of the vial in the same manner as described in relation to the first embodiment.

The dispensed condition of the device is seen in FIG. 12, with the head 119 of the pusher rod having pushed the vial holder 150 into the nozzle member 149. The spring 110 is again depressed and the end of the portion 108c is again located in the opening 113 of the cylinder 105. In other words, the pusher rod 108 has returned to the position seen in FIG. 9.

As the pusher rod 108 is moved from the position seen in FIG. 11 to the position seen in FIG. 12, the tapered portion 112 is forced through the arms of the clip spring 121b, which arms then spring back into the annular recess 120b of the pusher rod 108. Meanwhile, the clip spring 121a, which was open by removal of the cap 148, moves down the portion 108a of the pusher rod as that portion moves up through its arms.

After dispensing of the pharmaceutical substance, the nozzle unit 103 can be removed from the cylinder 105 for disposal. To remove the nozzle unit 103, the resilient skirt wings 156 are squeezed together by the user's finger and thumb in order to disengage the lips 157 from under the shoulders 168 of the rim 104. The nozzle member can then be gripped, lifted off and discarded. The cylinder 105 can now be put back in the carry case and the used nozzle unit preferably replaced by a fresh nozzle unit.

For completeness, the operation of the device will now briefly be described again. On sensing the onset of a migraine attack, the user will open the carry case and remove the cylinder assembly and one nozzle unit. That nozzle unit is then pushed onto the cylinder until the skirt wings have engaged under the rim of the cylinder, the legs of the cap releasing the spring which holds the pusher rod, the end of the pusher rod then being urged out of the cylinder by the spring. Next, the cap is pulled off which opens the other clip spring so that the pusher rod is free to move back into the cylinder, against the action of the spring. The device is placed in position, in the user's nasal cavity and depression of the end of pusher rod drives the vial holder into the nozzle member to dispense the contained substance through the nozzle opening. The nozzle member is then removed and disposed of. As with the first embodiment, the device of this embodiment is very easy to use and can be operated in a reliable and straightforward fashion to quickly and efficiently dispense a single dose of pharmaceutical substance, as and when the need arises.

The device also includes a number of security features to ensure that it is operated in the intended fashion. In particular, the following features are included.

1. The legs of the cap are required for the pusher rod to be brought from its dormant position to its actuation position. Thus, only a nozzle unit with a protective cap in place can be used to prime the device. Once the cap has been removed from the nozzle member, it cannot easily be refitted. Thus, there is little or no possibility of the device being operated in combination with a nozzle member which has previously been used.
2. Until the cap is removed, the pusher rod is blocked by one of the clip springs. The pusher rod is only freed upon removal of the cap so that there is no possibility of the device being discharged with the cap in place. The opportunity for accidental actuation, before the nozzle member is correctly placed in the nasal cavity, is thus limited.

It will be understood that the above advantages of the embodiment of FIGS. 7 to 12 are similar to those of the embodiment of FIGS. 1 to 6. Both embodiments thus present a dispensing device which is both easy and safe to use.

The component parts of the devices illustrated above are moulded from a suitable plastics material. For example, the cylinder, pusher rod and sleeve can be formed of ABS (Acrylonitrile Butadiene Styrene), while the nozzle member might be formed of polypropylene. The springs are formed of steel.

The invention claimed is:

1. A device for dispensing a pharmaceutical substance comprising:
    a disposable unit comprising a dose of the pharmaceutical substance, and a protective cap; and
    a body member on which the unit is removably mountable, the body member comprising an actuation member for dispensing the pharmaceutical substance from the unit, the actuation member being movable between a retracted position and an advanced position in which the pharmaceutical substance is dispensed;
    wherein the protective cap has at least one surface configured to operatively engage the body member such that the act of mounting the disposable unit on the body member moves the actuation member from the advanced to the retracted position.

2. A dispensing device according to claim 1, wherein the surface is on at least one depending leg of the protective cap.

3. A dispensing device according to claim 2, wherein the surface is at the end of the at least one depending leg of the protective cap.

4. A dispensing device according to any preceding claim 1, wherein the surface contacts the actuation member to move the actuation member from the advanced position to the retarded position upon mounting of the protective cap on the body member.

5. A dispensing device according to any preceding claim 1, wherein the protective cap has a blocking part which blocks movement of the actuation member from the retracted position to the advanced position, until removal of the cap.

6. A dispensing device according to claim 5, wherein the body member is formed in two parts, one part being slidably movable within the other and wherein the device is actuated at least partly by the sliding movement of the two parts, the said blocking part of the protective cap blocking the sliding movements of the two parts.

7. A dispensing device according to claim 6, wherein the blocking part is a protruding wing of the protective cap.

8. A dispensing device according to any of claims 1, wherein the body member includes a first blocking member which can hold the actuation member in the advanced position, the said surface of the protective cap acting on the blocking member to release the actuation member which in turn is movable under a resilient force to the retracted position.

9. A dispensing device according to claim 8, wherein the body member includes a second blocking member which can hold the actuation member in its retracted position, the second blocking member releasing the actuation member upon removal of the protective cap.

10. A dispensing device according to claim 8, wherein the blocking member is a spring which has an open position which releases the actuation member and a closed position which blocks the actuation member.

11. A dispensing device according to claim 10, wherein the surface is on at least one depending leg of the protective cap and wherein the spring has two arms which can be moved apart by the at least one leg of the protective cap as the unit is brought into mounting engagement on the body member.

12. A dispensing device according to any preceding claim 1, wherein the actuation member includes an indicating part which is visible on the outside of the body member, the indicating part thus indicating the position of the actuation member.

13. A dispensing device according to any preceding claim 1, wherein the body member has at the end on which the disposable unit is mountable laterally extending shoulders, the shoulders configured to receive depending wings of the disposable unit when the unit is mounted on said end of the body member.

14. A dispensing device according to any preceding claim 1, wherein the disposable unit includes a nozzle member for insertion in a user's nasal cavity and wherein the body member is generally cylindrical with the disposal unit mounted at one end and with the actuation member being movable along the axis of the cylinder between its advanced and retracted positions.

15. A dispensing device according to any preceding claim 1, wherein the disposable unit includes a unit dose of the pharmaceutical substance which is the only unit dose in the disposable unit.

16. A dispensing device according to any preceding claim 1, wherein the protective cap is removably mounted on the disposable unit.

17. A dispensing device according to any preceding claim 1, wherein the disposable unit is removably mounted on the body member.

18. A dispensing device according to any preceding claim 1, wherein the disposable unit is one of a set of such disposable units.

* * * * *

UNITED STATES PATENT AND TRADEMARK OFFICE
CERTIFICATE OF CORRECTION

| | |
|---|---|
| PATENT NO. | : 7,258,119 B2 |
| APPLICATION NO. | : 10/474493 |
| DATED | : August 21, 2007 |
| INVENTOR(S) | : Paolo Mazzoni |

It is certified that error appears in the above-identified patent and that said Letters Patent is hereby corrected as shown below:

Column 3, Lines 54-59 - should read:
-- The lower end of the cylindrical portion 26, below the floor 27 has longitudinal slots thus forming clip arms 29. The inner cylindrical portion 26 is for receiving the lower portion 8b of the pusher rod 8, the head 23 of the lower portion 8b being able to clip over the ends of the clip arms 29 of the retention clip 9. --

Claim 1 - Column 12, Line 46 - should read:
-- advanced position to the retracted position --

Claim 4 - Column 12, Line 52 - should read:
-- 4. A dispensing device according to claim --

Claim 4 - Column 12, Line 55 - should read:
-- the retracted position upon mounting of the protective cap on --

Claim 5 - Column 12, Line 57 - should read:
-- 5. A dispensing device according to claim --

Claim 8 - Column 13, Line 3 - should read:
-- 8. A dispensing device according to claim --

Claim 8 - Column 13, Line 6 - should read:
-- position, the surface of the protective cap acting on the --

Claim 12 - Column 13, Line 25 - should read:
-- 12. A dispensing device according to claim --

Claim 13 - Column 14, Line 1 - should read:
-- 13. A dispensing device according to claim --

Claim 14 - Column 14, Line 7 - should read:
-- 14. A dispensing device according to claim --

Claim 15 - Column 14, Line 14 - should read:
-- 15. A dispensing device according to claim --

Claim 16 - Column 14, Line 18 - should read:
-- 16. A dispensing device according to claim --

UNITED STATES PATENT AND TRADEMARK OFFICE
CERTIFICATE OF CORRECTION

PATENT NO. : 7,258,119 B2
APPLICATION NO. : 10/474493
DATED : August 21, 2007
INVENTOR(S) : Paolo Mazzoni It is certified that error appears in the above-identified patent and that said Letters Patent is hereby corrected as shown below:

Claim 17 - Column 14, Line 21 - should read:
 -- 17. A dispensing device according to claim --

Claim 18 - Column 14, Line 24 - should read:
 -- 18. A dispensing device according to claim --

Signed and Sealed this

Sixteenth Day of December, 2008

JON W. DUDAS
*Director of the United States Patent and Trademark Office*